US009989462B2

(12) United States Patent
Lumpkin et al.

(10) Patent No.: US 9,989,462 B2
(45) Date of Patent: Jun. 5, 2018

(54) LASER NOISE DETECTION AND MITIGATION IN PARTICLE COUNTING INSTRUMENTS

(71) Applicant: PARTICLE MEASURING SYSTEMS, INC., Boulder, CO (US)

(72) Inventors: James Lumpkin, Loveland, CO (US); Matthew Melton, Boulder, CO (US)

(73) Assignee: PARTICLE MEASURING SYSTEMS, INC., Boulder, CO (US)

(*) Notice: Subject to any disclaimer, the term of this patent is extended or adjusted under 35 U.S.C. 154(b) by 0 days. days.

(21) Appl. No.: 15/088,679

(22) Filed: Apr. 1, 2016

(65) Prior Publication Data
US 2016/0356711 A1 Dec. 8, 2016

Related U.S. Application Data

(60) Provisional application No. 62/142,141, filed on Apr. 2, 2015, provisional application No. 62/205,239, filed on Aug. 14, 2015.

(51) Int. Cl.
G01N 21/00 (2006.01)
G01N 21/53 (2006.01)
(Continued)

(52) U.S. Cl.
CPC ......... G01N 21/53 (2013.01); G01N 15/1429 (2013.01); G01N 15/1459 (2013.01);
(Continued)

(58) Field of Classification Search
CPC ............... G01N 21/53; G01N 15/1429; G01N 15/1459; G01N 2015/0038;
(Continued)

(56) References Cited

U.S. PATENT DOCUMENTS 3,851,169 A 11/1974 Faxvog
4,348,111 A 9/1982 Goulas et al.
(Continued)

OTHER PUBLICATIONS

Search Report and Written Opinion, dated Jun. 30, 2016, corresponding to International Application No. PCT/US16/25565 (filed Apr. 1, 2016), a related application, 9 pp.
(Continued)

Primary Examiner — Hina F Ayub
(74) Attorney, Agent, or Firm — Lathrop Gage LLP

(57) ABSTRACT

This invention relates to optical particle counters and methods capable of effectively distinguishing signals generated from particle light scattering from sources of noise. Embodiments of the invention, for example, use multisensory detector configurations for identifying and distinguishing signals corresponding to fluctuations in laser intensity from signals corresponding to particle light scattering for the detection and characterization of submicron particles. In an embodiment, for example, methods and systems of the invention compare signals from different detector elements of a detector array to identify and characterize noise events, such as noise generated from laser intensity instability, thereby allow for the detection and characterization of smaller particles. The system and methods of the present invention, thus, provide an effective means of reducing false positives caused by noise or interference while allowing for very sensitive particle detection.

29 Claims, 7 Drawing Sheets

(51) Int. Cl.
*G01N 15/14* (2006.01)
*G01N 15/00* (2006.01)
*G01N 15/10* (2006.01)

(52) U.S. Cl.
CPC ............... *G01N 2015/0038* (2013.01); *G01N 2015/0053* (2013.01); *G01N 2015/1006* (2013.01); *G01N 2015/1488* (2013.01)

(58) Field of Classification Search
CPC ... G01N 2015/0053; G01N 2015/1006; G01N 2015/1488
USPC .......................................................... 356/338
See application file for complete search history.

(56) References Cited

U.S. PATENT DOCUMENTS

| | | | |
|---|---|---|---|
| 4,728,190 A | 3/1988 | Knollenberg | |
| 4,957,363 A | 9/1990 | Takeda et al. | |
| 5,037,202 A * | 8/1991 | Batchelder | G01N 15/0205 356/335 |
| 5,085,500 A | 2/1992 | Blesener | |
| 5,121,988 A | 6/1992 | Blesener et al. | |
| 5,282,151 A | 1/1994 | Knollenberg | |
| 5,463,460 A * | 10/1995 | Fishkin | G01N 21/53 356/339 |
| 5,467,188 A | 11/1995 | Miyashita | |
| 5,642,193 A | 6/1997 | Girvin et al. | |
| 5,864,399 A | 1/1999 | Girvin et al. | |
| 5,880,474 A | 3/1999 | Norton et al. | |
| 5,920,388 A | 7/1999 | Sandberg et al. | |
| 5,946,092 A | 8/1999 | DeFreez et al. | |
| 6,061,132 A | 5/2000 | Girvin et al. | |
| 6,859,277 B2 | 2/2005 | Wagner et al. | |
| 7,002,682 B2 | 2/2006 | Girvin et al. | |
| 7,030,980 B1 | 4/2006 | Sehler et al. | |
| 7,053,783 B2 | 5/2006 | Hamburger et al. | |
| 7,315,372 B1 * | 1/2008 | Billard | G01N 15/1434 356/338 |
| 7,456,960 B2 | 11/2008 | Cerni et al. | |
| 7,755,760 B2 | 7/2010 | Nakajima et al. | |
| 7,973,929 B2 * | 7/2011 | Bates | G01N 15/1012 356/336 |
| 8,013,994 B1 * | 9/2011 | Vattiat | G01J 5/0014 219/121.36 |
| 8,748,183 B2 | 6/2014 | Durack et al. | |
| 2006/0132770 A1 * | 6/2006 | Girvin | G01N 15/1459 356/338 |
| 2006/0244965 A1 * | 11/2006 | Ichijo | G01N 15/0205 356/338 |
| 2009/0244536 A1 * | 10/2009 | Mitchell | G01N 15/1459 356/343 |
| 2013/0224726 A1 * | 8/2013 | Durack | C12N 5/0612 435/3 |
| 2014/0285802 A1 | 9/2014 | Shimmura et al. | |

OTHER PUBLICATIONS

Liu et al. (Dec. 2005) "Detection of particle sources with directional detector arrays and a mean-difference test," IEEE Transactions on Signal Processing. 53(12):4472-4484.

Wu et al. (Sep. 2002) "Reduction of Fringe Noise in Wavelength Modulation Spectroscopy Using a One-Dimensional Focal Plane Array," Optical Review. 9(5):189-192.

International Preliminary Report on Patentability dated Oct. 3, 2017, for International Patent Application No. PCT/US2016/025565.

* cited by examiner

LASER NOISE DETECTION AND MITIGATION IN PARTICLE COUNTING INSTRUMENTS

CROSS-REFERENCE TO RELATED APPLICATIONS

This application claims the benefit of and priority to U.S. Provisional Application No. 62/142,141, filed Apr. 2, 2015, and U.S. Provisional Application No. 62/205,239, filed Aug. 14, 2015, both of which are hereby incorporated by reference in their entirety to the extent non inconsistent with the disclosure herein.

BACKGROUND OF INVENTION

This invention is in the field of optical particle analyzers. In an embodiment, his invention relates generally to two-dimensional optical imaging-based methods and systems for detecting and characterizing particles in fluid samples. In an embodiment, this invention also relates generally to methods and systems for improving the sensitivity and versatility of optical particle analyzers and for extending device performance of these systems so as to accurately detect and characterize particles having small physical dimensions (e.g., less than 0.1 microns).

A large portion of the micro-contamination industry and clean manufacturing industries is reliant on the use of optical particle counters, such as are described in a large number of U.S. patents, including U.S. Pat. Nos. 3,851,169, 4,348,111, 4,957,363, 5,085,500, 5,121,988, 5,467,188, 5,642,193, 5,864,399, 5,920,388, 5,946,092, and 7,053,783. Particle counters are also described in U.S. Pat. Nos. 4,728,190, 6,859,277, and 7,030,980, 5,282,151, which are hereby incorporated by reference in their entirety.

Optical particle sensors and counters are useful in a variety of industrial applications including in semiconductor, pharmaceutical and microelectronics industries. In some industrial settings, optical particle sensors and counters provide an important tool for continuously monitoring the composition and purity of materials used in a process, for example, in the production of pharmaceutical products subject to stringent regulatory requirements relating to particulate contaminates. In other industrial settings, optical particle sensors and counters provide an important tool for providing quality control analysis, for example for off-line quality control checking of high quality photoresist and semiconductor materials. It is particularly advantageous to rapidly identify when a fluid is contaminated with unwanted particles so that the process can be stopped at an early stage, thereby avoiding wasteful manufacture of defective product. For example, in semi-conductor and other clean-room settings, or industries requiring sterile and pure production (e.g., pharmaceuticals), material fluids that are used to make the end products are continuously monitored to ensure adequate purity and that any unwanted particles suspended in the fluid is within an acceptable tolerance range. Aerosol particle counters are often used to measure air-born particle contamination in clean-rooms and clean zones. Liquid phase particle counters are often used to measure particulate contamination in pharmaceutical, water treatment and chemical processing industries.

The importance of particle monitoring sensors is reflected in the continuous and ongoing improvement and development of these devices to improve reliability and throughput, and to enable detection and characterization of particles having smaller sizes. In addition to limitations on sensitivity and particle sizing capability, state of the art optical particle counters are currently susceptible to problems relating to false counts generated when detector noise and/or signals resulting from processes other than optical scattering from particles are attributed to a particle detection event. The occurrence of false counts adversely impacts accuracy and sensitivity of the systems. Furthermore, the occurrence of false counts also impedes the capability of optical particle analyzers to accurately detect and characterize particles having small physical dimensions (e.g., less than 0.5 microns). As a result, design strategies for avoiding or suppressing false counts in optical particle counters and analyzers is a priority in development of the next generation of these devices.

As particle sensing is applied to monitor and characterize particles of smaller physical dimensions, there is an increasing need for particle counter systems that are able to effectively distinguish sources of noise from particle scattering so as to achieve greater sensitivity and accuracy.

SUMMARY OF THE INVENTION

This invention relates to optical particle counters and methods capable of effectively distinguishing signals generated from particle light scattering from sources of noise. Embodiments of the invention, for example, use multisensory detector configurations for identifying and distinguishing signals corresponding to fluctuations in laser intensity from signals corresponding to particle light scattering for the detection and characterization of submicron particles. In an embodiment, for example, methods and systems of the invention compare signals from different detector elements of a detector array to identify and characterize noise events, such as noise generated from laser intensity instability, thereby allowing for the detection and characterization of smaller particles. The system and methods of the present invention, thus, provide an effective means of reducing false positives caused by noise or interference while allowing for very sensitive particle detection.

In some embodiments, the systems and methods of the invention achieve effective characterization of detector signals on the basis of the spatially distribution characteristics of scattered and/or emitted light, as implemented using a detector configuration comprising a plurality of detectors to independently view different portions of a viewing region. In some embodiments, the systems and methods of the invention achieve effective characterization of detector signals on the basis of temporal characteristics upon, during and/or after the detection of a laser noise event. The systems and methods provided are highly versatile and may be used for the detection and characterization of a range of particles, including particles with small physical dimensions (e.g., optionally <1 micron, optionally <0.5 microns), in a wide range of fluids, such as ultrapure water and process chemicals.

In an aspect, the present invention provides a method for detecting particles in a fluid flow, the method comprising the step of: (i) providing the fluid flow having the particles; (ii) exposing the fluid flow to a beam of electromagnetic radiation from a laser, thereby generating scattered or emitted electromagnetic radiation; (iii) collecting and directing the scattered or emitted electromagnetic radiation from a viewing region onto a plurality of detector elements; wherein each detector element is positioned to receive scattered or emitted electromagnetic radiation from a different portion of the viewing region; (iv) detecting the electromagnetic radiation directed onto the plurality of detector elements, wherein each of the detector elements generates independent output signals; (v) comparing output signals from at least two different detector elements to discriminate output signals corresponding to a particle detection event from output signals corresponding to a laser noise event; and (vi) analyzing output signals corresponding to the detection event, thereby detecting the particles in the fluid flow. In an embodiment, for example, an increase in the magnitude of the output signals of at least two of the detector elements, optionally at least two non-adjacent detector elements, is indicative of the laser noise event. In an embodiment, an increase in the magnitude of the output signals of only a single detector element, or a subset of adjacent detector elements, is indicative of the particle detection event. As used herein, adjacent detector elements in array are neighboring detector elements in an array (e.g., 1D or 2D array), for example laterally or longitudinally neighboring detector elements. As used herein, adjacent detector elements may, however, be spaced from each other, for example, by space on the detector not functioning as an optical detector element, such as space not comprising an active detector area or comprising an active detector area that is not being used for optical measurements. In some embodiments, adjacent detector elements are neighboring pixels on an array.

In an embodiment, for example, the step of collecting and directing the scattered or emitted electromagnetic radiation from the viewing region is provided using a system of optics for focusing the scattered or emitted electromagnetic radiation from the viewing region, such as within a flow cell housing a flow of fluid, on to the plurality of detector elements. In an embodiment, the physical dimensions, positions or both of detector elements are such that only a subset of detector elements of the plurality receives the scattered or emitted electromagnetic radiation corresponding to the particle detection event. In an embodiment, the physical dimensions, positions or both of detector elements are such that all the detector elements of the plurality receive the scattered or emitted electromagnetic radiation corresponding to the laser noise event.

In an embodiment, for example, the plurality of detectors comprise a detector array positioned in optical communication with the system of optics such that each element of the array receives scattered or emitted electromagnetic radiation from a different portion of the viewing region. In embodiments, for example, the detector array is a one dimensional array comprising 2 to 100 detector elements, and optionally for some embodiments 2 to 20 detector elements. In embodiments, each of the detector elements of the one dimensional array independently has an active area characterized by lateral dimensions selected from the range of 100 µm to 1000 µm, and optionally 410 µm to 440 µm. In embodiments, for example, adjacent detector elements of the one dimensional array are separated from each other by a distance selected from the range of 50 µm to 150 µm, optionally for some applications 60 µm to 90 µm. In embodiments, the laser is a solid state laser or diode laser. In embodiments, for example, the detector array is a two dimensional array comprising 2 to 1000 detector elements, and optionally for some embodiments 2 to 400 detector elements.

In an embodiment, for example, the laser noise event corresponds to a change in the radiative output (e.g., intensity, power, flux, etc.) of the laser, thereby generating scattered or emitted electromagnetic radiation from the viewing region having a substantially uniform spatial distribution of intensities (e.g., a distribution of intensities that are within 30% of each other, optionally that are within 10% of each other). In an embodiment, the particle detection event corresponds to a particle passing through beam of electromagnetic radiation, thereby generating scattered or emitted electromagnetic radiation from the viewing region having a nonuniform spatial distribution of intensities. In an embodiment, for example, the step of comparing output signals from at least two different detector elements comprises characterizing the spatial distribution of intensities of the scattered or emitted electromagnetic radiation to discriminate output signals corresponding to a particle detection event from output signals corresponding to a laser noise event.

In an embodiment, for example, the method further comprises identifying the particle detection event. In an embodiment, the particle detection event is identified when the output signals of only a single detector element or subset of adjacent detector elements is independently equal or greater than a threshold value. In an embodiment, the threshold value for a given detector element is equal to 1.3:1 to 3.0:1, optionally for some applications 1.5:1 to 2.0:1, times the standard deviation of the noise of the given detector element of said array.

In an embodiment, for example, the method further comprises identifying the laser noise event. In an embodiment, the laser noise event is identified when the output signals of each of at least two non-adjacent detector elements is independently equal or greater than a threshold value, such as 2, 3, 4 or 5 non-adjacent detector elements. In an embodiment, the threshold value is independently set for each detector element. In an embodiment, for example, the threshold value for a given detector element is equal to 1.3:1 to 3.0:1, optionally for some applications 1.5:1 to 2.0:1, times the standard deviation of the noise of the given detector element of the array.

In an embodiment, for example, the method further comprises, upon identification of a laser noise event, monitoring the output signals for all detector elements to identify a change in output values for at least two detector elements independently greater than or equal to a factor of 1.5:1 to 2.0:1. In an embodiment, the method further comprises the steps of: (i) storing the output signals for all detector elements for a selected time period, such as a time period selected from the range of 8 ms to 40 ms; and (ii) analyzing the stored output signals in the event that no laser noise event is identified or discarding the stored output signals in the event that the laser noise event is identified. In an embodiment, for example, the method further comprises, upon identification of a laser noise event, waiting for a selected time period, such as a time period selected from the range 10 ms to 50 ms, prior to identifying a particle detection event.

In an embodiment, for example, the particles are characterized by cross sectional dimensions greater than or equal to 20 nm. In embodiments, the fluid is a liquid or a gas. In embodiments, for example, the fluid is ultrapure water, Sulfuric Acid ($H_2SO_4$), Hydrofluoric Acid (HF), Hydrochloric Acid (HCl), Ammonium Hydroxide ($NH_4OH$), Hydrogen Peroxide ($H_2O_2$) or Isopropyl Alcohol ($C_3H_7OH$). In an embodiment, the method further comprises a step of counting the particles, wherein the step of comparing output signals from at least two different detector elements to discriminate output signals corresponding to the particle detection event from output values corresponding to the laser noise event enables a decrease in the occurrence of false counts, for example, wherein particles are counted on the basis of a size criteria, such as width, radius, etc. In an embodiment, for example, the method further comprises controlling a temperature of said laser to reduce laser noise, wherein said controlling is performed with a thermoelectric cooler (TEC). In an embodiment, for example, the method further comprises determining the size of the particles.

In an aspect, the present invention provides an optical particle counter comprising: (i) a laser for generating a beam of electromagnetic radiation; (ii) a flow chamber for flowing a fluid containing particles along a flow direction and through the beam of electromagnetic radiation, thereby generating scattered or emitted electromagnetic radiation; (iii) an optical collection system for collecting and directing scattered or emitted electromagnetic radiation from a viewing region onto a plurality of detector elements; (iv) the detector elements for detecting the electromagnetic radiation and generating independent output signals; and wherein each detector element is positioned to receive scattered or emitted electromagnetic radiation from a different portion of the viewing region; and (v) a signal processing system, for example a complex programmable logic device such as a processor and/or microcontroller, operationally connected to the detector elements for: comparing output signals from at least two different detector elements to discriminate output signals corresponding to a particle detection event from output signals corresponding to a laser noise event; and analyzing the output values corresponding to the detection event.

In an aspect, the invention provides a method of distinguishing particle scattering from laser noise in an optical particle analyzer, the method comprising the steps of: (i) providing a fluid flow having particles to the optical particle analyzer; (ii) exposing the fluid flow to a beam of electromagnetic radiation from a laser, wherein interaction between the fluid flow and the beam generates scattered or emitted electromagnetic radiation; (iii) collecting and directing the scattered or emitted electromagnetic radiation from a viewing region onto a plurality of detector elements; wherein each detector element is positioned to receive the scattered or emitted electromagnetic radiation of from a different portion of the viewing region; (iv) detecting the electromagnetic radiation directed onto the plurality of detector elements, wherein each of the detector elements generates independent output signals; and (v) comparing output signals from at least two nonadjacent different detector elements to discriminate output signals corresponding to a particle detection event from output signals corresponding to a laser noise event.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

DETAILED DESCRIPTION OF THE INVENTION

Figure 1:
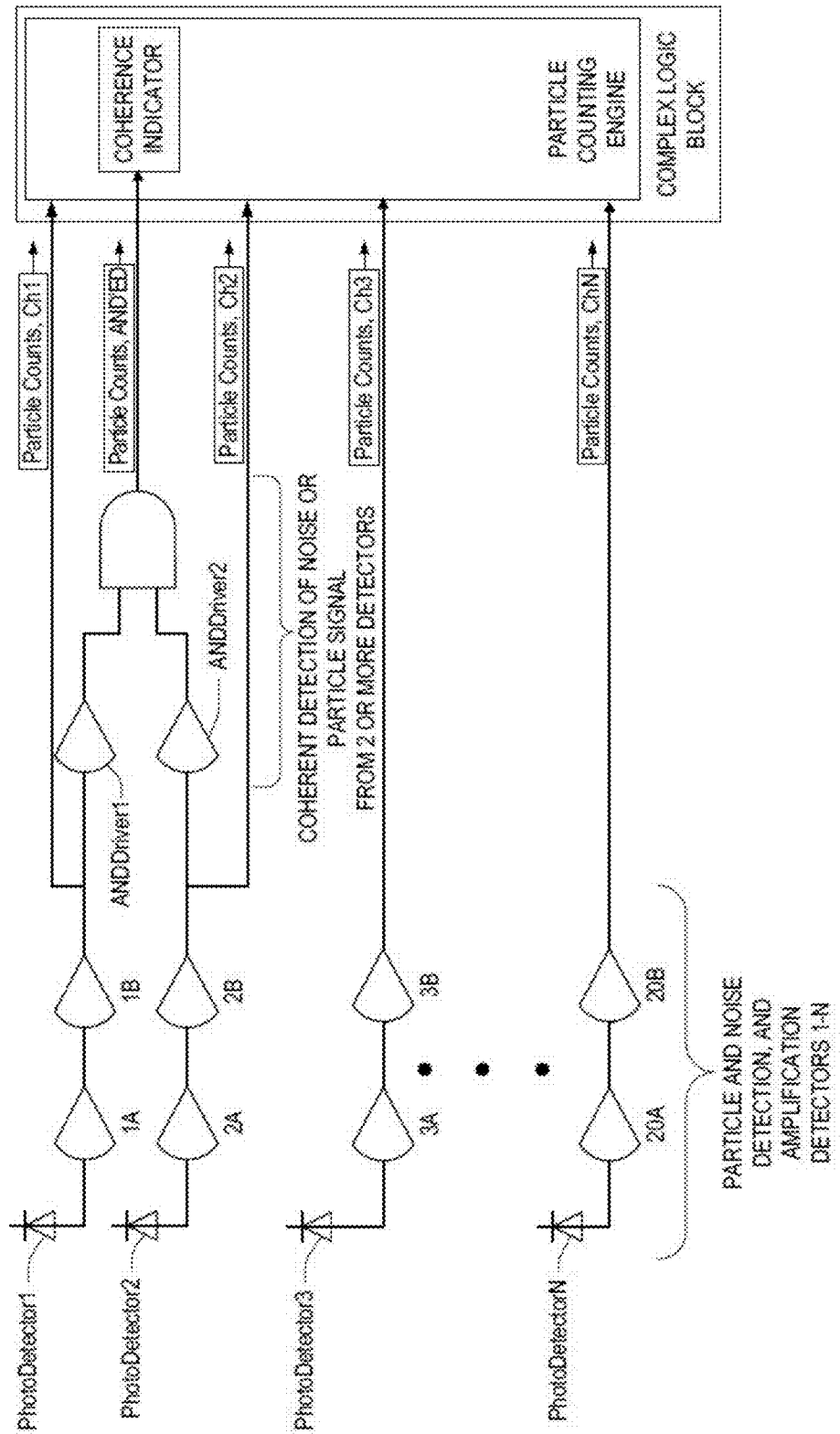
FIG. 1. Provides a schematic diagram illustrating an example of an electronic circuit diagram useful for implementation of the present systems and methods using a multisensory detector configuration.

In general the terms and phrases used herein have their art-recognized meaning, which can be found by reference to standard texts, journal references and contexts known to those skilled in the art. The following definitions are provided to clarify their specific use in the context of the invention.

"Flow direction" refers to an axis parallel to the direction the bulk of a fluid is moving when a fluid is flowing. For fluid flowing through a straight flow cell, the flow direction is parallel to the path the bulk of the fluid takes. For fluid flowing through a curved flow cell, the flow direction may be considered tangential to the path the bulk of the fluid takes.

"Beam propagation axis" refers to an axis parallel to the direction of travel of a beam of electromagnetic radiation.

"Cross sectional profile" refers to a profile formed by a plane cutting through an object at a right angle to an axis of propagation or travel. For example the cross sectional profile of a beam of electromagnetic radiation is a profile of the beam formed by a plane perpendicular to the beam propagation axis. The cross sectional profile of a flow cell is a profile of the flow cell formed by a plane perpendicular to the flow direction.

"Optical communication" refers to components which are arranged in a manner that allows light to transfer between the components.

"Optical axis" refers to a direction along which electromagnetic radiation propagates through a system.

"Optical source" refers to a device or device component that is capable of delivering electromagnetic radiation to a sample. The term is not limited to visible radiation, such as by a visible light beam, but is used in a broad sense to include any electromagnetic radiation. The optical source may be embodied as a laser or laser array, such as a diode laser, diode laser array, diode laser pumped solid state laser, LED, LED array, gas phase laser, solid state laser, to name a few examples.

The term "electromagnetic radiation" and "light" are used synonymously in the present description and refer to waves of electric and magnetic fields. Electromagnetic radiation useful for the methods of the present invention include, but is not limited to ultraviolet light, visible light, infrared light, or any combination of these having wavelengths between about 100 nanometers to about 15 microns.

The expression "detecting a particle" broadly refers to sensing, identifying the presence of and/or characterizing a particle. In some embodiments, detecting a particle refers to counting particles. In some embodiments, detecting a particle refers to characterizing and/or measuring a physical characteristic of a particle, such as diameter, cross sectional dimension, shape, size, aerodynamic size, or any combination of these.

"Particles" refers to small objects which are often regarded as contaminants. A particle can be any material created by the act of friction, for example when two surfaces come into mechanical contact and there is mechanical movement. Particles can be composed of aggregates of material, such as dust, dirt, smoke, ash, water, soot, metal, minerals, or any combination of these or other materials or contaminants. "Particles" may also refer to biological particles, for example, viruses, spores and microorganisms including bacteria, fungi, archaea, protists, other single cell microorganisms and specifically those microorganisms having a size on the order of 1-15 µm. A particle may refer to any small object which absorbs or scatters light and is thus detectable by an optical particle counter. As used herein, "particle" is intended to be exclusive of the individual atoms or molecules of a carrier fluid, for example water molecules, process chemical molecules, oxygen molecules, helium atoms, nitrogen molecules, etc. Some embodiments of the present invention are capable of detecting, sizing, and/or counting particles comprising aggregates of material having a size greater than 10 nm, 20 nm, 30 nm, 50 nm, 100 nm, 500 nm, 1 µm or greater, or 10 µm or greater. Specific particles include particles having a size selected from 20 nm to 50 nm, 50 nm to 50 µm, a size selected from 100 nm to 10 µm, or a size selected from 500 nm to 5 µm.

The terms "optical particle counter" and "particle counter" are used interchangeably herein and refer to systems capable of detecting particles suspended in a fluid, systems capable of determining the sizes of particles suspended in a fluid, systems capable of counting particles suspended in a fluid, systems capable of classification of particles suspended in a fluid, or any combination of these. A typical liquid or aerosol optical particle counter is comprised of several components, such as a source for generating a beam of electromagnetic radiation, optics for directing the beam into a region where a fluid sample is flowing, for example a liquid or gas flowing through a flow cell. A typical optical particle counter is also comprised of a photodetector, such as a two-dimensional optical detector, and collection optics for detecting electromagnetic radiation which is scattered by or emitted by particles which pass through the beam, and other electronics for the processing and analysis of electrical signals produced by the photodetector including current to voltage converters and signal filtering and amplification electronics. An optical particle counter may also be comprised of a pump for creating a flow for introducing a fluid sample to the detection region where the electromagnetic beam is present.

"Fluid communication" refers to the arrangement of two or more objects such that a fluid can be transported to, past, through or from one object to another. For example, in some embodiments two objects are in fluid communication with one another if a fluid flow path is provided directly between the two objects. In some embodiments, two objects are in fluid communication with one another if a fluid flow path is provided indirectly between the two objects, such as by including one or more other objects or flow paths between the two objects. For example, in one embodiment, the following components of a particle impactor are in fluid communication with one another: one or more intake apertures, an impact surface, a fluid outlet, a flow restriction, one or more pressure sensors, and/or a flow generating device. In one embodiment, two objects present in a body of fluid are not necessarily in fluid communication with one another unless fluid from the first object is drawn to, past and/or through the second object, such as along a flow path.

"Flow rate" refers to an amount of fluid flowing past a specified point or through a specified area, such as through intake apertures or a fluid outlet of a particle impactor. In one embodiment a flow rate refers to a mass flow rate, i.e., a mass of the fluid flowing past a specified point or through a specified area. In one embodiment a flow rate is a volumetric flow rate, i.e., a volume of the fluid flowing past a specified point or through a specified area.

The invention is further detailed in the following Examples, which are offered by way of illustration and are not intended to limit the scope of the invention in any manner.

EXAMPLE 1

Identification and Discrimination of Laser Noise Events Using a Multi-element Detector Configuration.

In embodiments of the present invention, when using multi-element photonic detectors for detection of submicron particles in fluids; liquid or aerosol, it is beneficial to utilize one or more of detector elements to distinguish between the very low signal level that is generated when a nano-size particle passes through the sampling region, and the increase in light level when the light source undergoes brief periods of positive light intensity fluctuations. In light scattering particle counters, as a particle passes thru the sampling region it generates an increase in light scattered signal above the background molecular scatter of the sample fluid. When the light source, which is typically a laser in state of the art particle counters, experiences a momentary unstable state, its light output can "burst" in output intensity. These bursts periods are typically referred to as laser noise. These momentary bursts can be interpreted as particle signals leading to "false" counts in the instruments reported data.

In the design of multi-element detector particle counters of embodiments of the invention, the optical system is designed in such a way that all elements are viewing separate portions of the sampling region, for example, separate regions along the length of the lasers focused light within a flow cell. When a particle passes through one region of the sample area, its scattered light will be viewed by the specific element or subset of adjacent elements viewing that area. As a whole, in some embodiments, the complete multi-element array is viewing substantially all components (e.g., ≥80%), and optionally all components, of the scattered laser light corresponding to in the viewing region. For very small particles, when a real particle passes through the viewing region and depending on where spatially it passes, a subset of the detector elements, and optional only one detector element, will see that particle (e.g., receiving a sufficient intensity of particle scattered light for measurement). When the laser light source experiences an unstable condition and it bursts, in contrast, a plurality of detector elements, and optional all elements, will see this increase in light intensity. By using one element as an indicator of laser light fluctuation or ANDing two or more elements together, a real particle's scattering signal can be distinguished from the laser's light. Furthermore, ANDing of the output signal from an independent detector that has been setup, through the use of a beam splitter, to view the full Gaussian or shaped beam of the laser, together with one of more of the elements from the multi-element array, can be used to distinguish between laser noise bursts and real particle signals.

Both Solid State Lasers and Diode lasers can experience unstable noise bursting when their cavity length changes due to changing temperature. Changes in Injection Current and Optical feedback can also cause lasers to go unstable and burst or Mode hope. By using the single element indicator or the multi-element ANDing, or the independent detector ANDed together with one or more of the elements from the multi-element detector, the false count rate for very high sensitivity, i.e., very small particle detection particle counters can be reduced to minimum levels. Without this multi-element detection scheme to detect the laser noise, in some instances the laser's noise signals becomes just as strong a small particle signals and one cannot be distinguished one from another.

Figure 3:
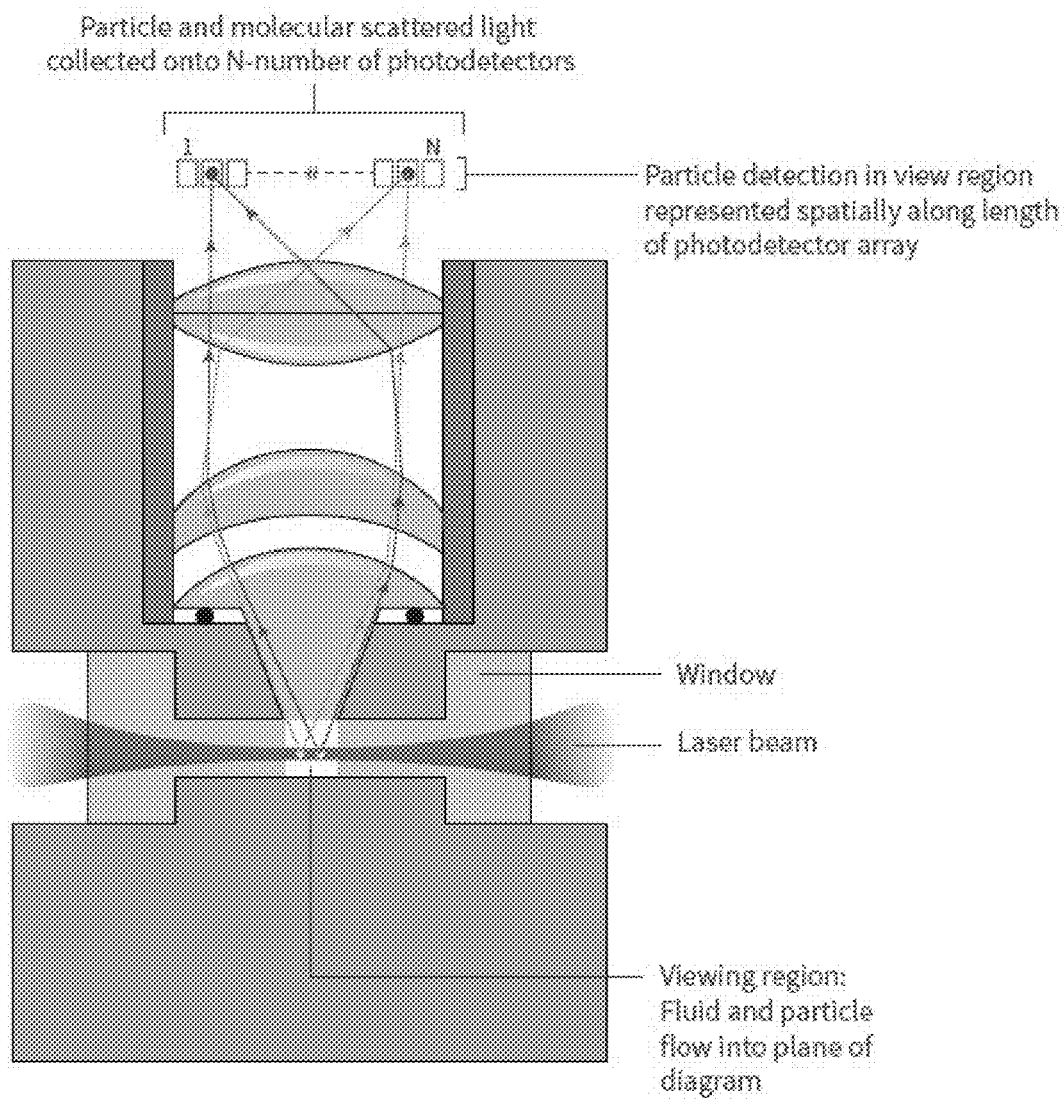
FIG. 3. Provides a schematic diagram illustrating an example flow cell and optical geometry useful in the present systems and methods.

FIG. 3 provides a schematic diagram illustrating an example flow cell and optical geometry useful in the present systems and methods. As shown in FIG. 3, a flow cell is provided having a pair of windows for passing a laser beam through the cell. A fluid flow is provided through the flow cell such that particles in the fluid pass through and interact with the laser beam. Scattered and/or emitted light from a viewing region within the flow cell is collected by a system of optics and imaged onto the active area of a one dimensional array detector (optionally a 2D array detector). As show in FIG. 3, the one dimensional array detector comprises a plurality of independent detector elements (1-N detectors) that are each are positioned to receive scattered and/or emitted radiation from a different portion of the viewing region. This optical geometry provides for only a subset of the detector elements of the array, and optionally a single detector element, to receive scattered light from a particle in the fluid having a sufficient intensity to result in identification and/or characterization of the particle. In contrast, a plurality of the detector elements in the one dimensional array, and optionally all detector elements, are positioned to receive scattered light from the viewing region corresponding to molecular scatter of the carrier fluid as well as other scattering processing in the flow cell. Accordingly, this optical geometry results in a plurality of detector elements, and optionally all detector elements, receiving and detecting scattered light resulting from a laser noise event, such as a variation in output intensity of the laser, for example due to mode hopping from a change in cavity dimensions due to a change in temperature.

FIG. 1 provides a schematic diagram illustrating an example of an electronic circuit diagram useful for implementation of the present systems and methods using a multisensory detector configuration. As shown in FIG. 1, photodetectors 1 through N, make-up an array detector that as a whole, view a length of a laser's focused light beam which has been steered through a fluid sampling region. Individually, Photodetector's 1-N, view their own portions along the length of the viewed laser beam. In the absence of particles, each of the Photodetectors 1 through N will witness the same low level of light scattering which is a combination of the fluid's molecular scatter and the laser's light intensity variation. As the particles are carried through the sample region, they are spaced from one another and the scattered light generated by each particle is collected by the individual Photodetector viewing the area where the particle passed. The scattering photons generated from very small particles and collected by the Photodetectors require subsequent amplification with appropriate Bandwidth tuning; labeled as "Particle and Noise Detection and Amplification Detectors 1-N" in FIG. 1. Output signals from the individual Photodetectors are passed through to a Complex Logic Block and it's software driven Particle Counting Engine.

Additionally, two or more of the amplified Photodetector output signals are combined to form an AND function, whose output signal is passed through to the Complex Logic Block. The AND function, labeled "Coherent Detection of Noise or Particle Signal From Two Or More Detectors" is used to detect when the laser's light intensity, which is common and seen across all Photodetectors, experiences an increase in intensity. The output, labeled "Coherence Indicator" from the AND function will only be present when there is a positive shift in intensity of the laser's light, seen concurrently by both Photodetectors. In general, the Photodetector array, the associated amplification and power driving electronics and Complex Logic are combined on a single Printed circuit Board to minimize electronic circuit noise.

Detecting particles by light scattering very much involves handling real time events. The time window to capture the events is generally in the millisecond domain as particles travel through the active region of the laser beam.

Because of the real time nature of light scattering, historically this has been handled using analog electronics that detects when the scattered light has crossed a programmable threshold. Introducing fast programmable logic into the system allows additional processing steps to occur. Provided are examples of the additional processing employed to date include correlating multiple detectors and better determination of particle sizes based on captured energy from the scattering. The systems and method use fast complex digital logic in particle detection and quantify the raw detection signals along with extra information from the detector array.

In some cases, it is preferential not to allow the real time particle detections to be processed until it had been determined if the system was subject to noise. The determination of noise often was several milliseconds after the initial detections occurred. This led to employing a pipelining scheme to hold these real time events for future processing. Obviously, these events cannot be delayed indefinitely since more potential events can be arriving every few milliseconds. The provided systems and methods delay the final decision to count the particles for a short period of time while an evaluation occurs to determine if noise is present in the system.

Figure 2:
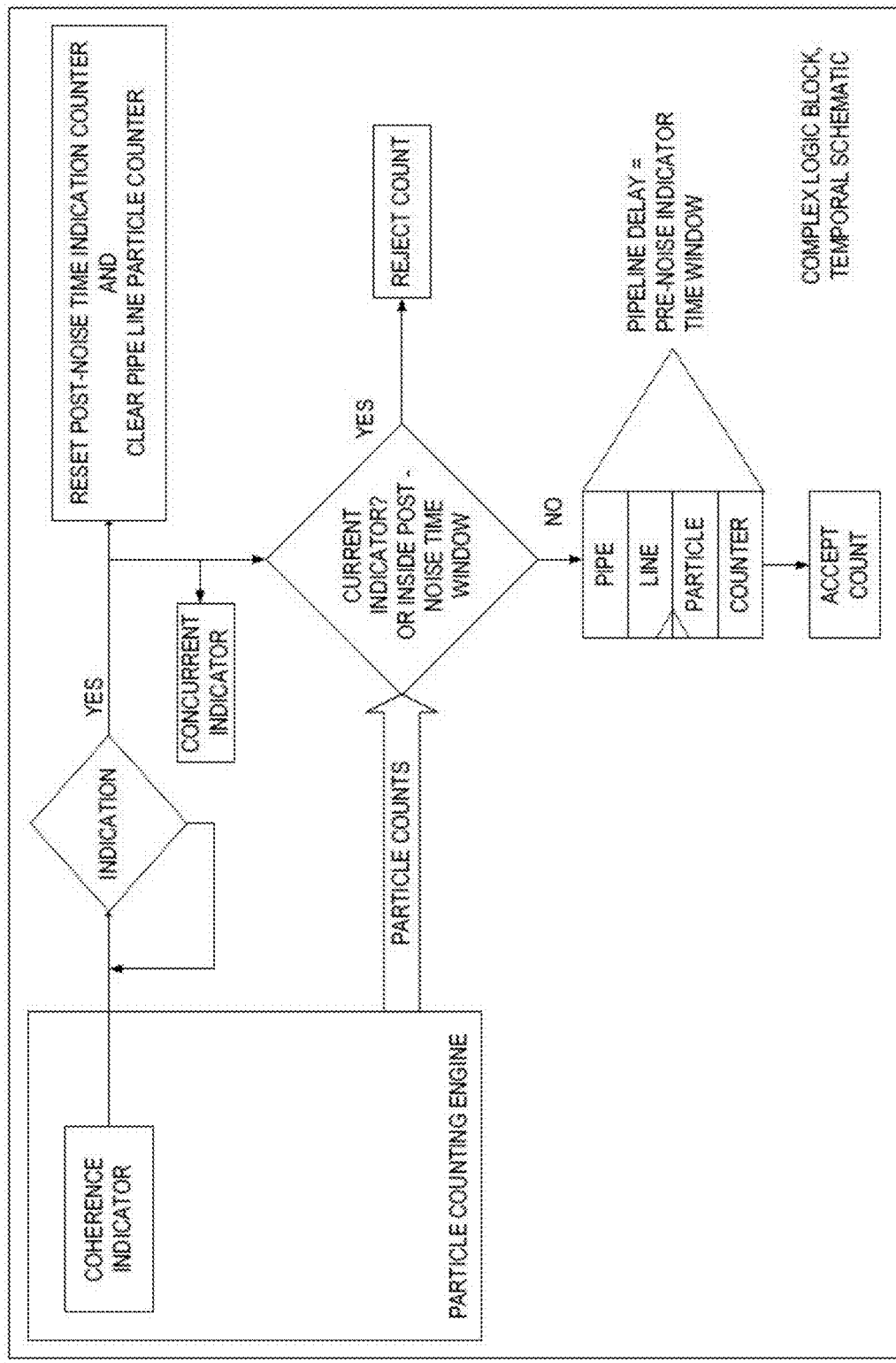
FIG. 2. Provides a flow diagram of an example analysis method for the identification and differentiation of a laser noise event useful in the present systems and methods.

FIG. 2 provides a flow diagram of an example analysis method for the identification and differentiation of a laser noise event useful in the present systems and methods. Particularly, a flow diagram for handling the Coherence indicator and particle count events in a Complex Programmable logic Block is shown. Because the increase in laser light intensity from a laser noise event evolves temporally, this process can be viewed in some ways as analogous to a volcanic eruption where there is a build-up in activity before the actual eruption and then a tailing-off of activity following the eruption itself, means there is an option to "pipeline" particle counts over a selected period before a laser noise event, such as from between 8 ms and 40 ms, and reject them if the noise event happens within this time window, and also a need to hold-off acceptance of particle counts following a laser noise event by a programmed time, such as between 10 ms to 50 ms. In FIG. 2, there are three functions running simultaneously. 1) When there is laser noise, as indicated by the Coherence Indicator, any concurrent particle events or particle counts currently in the Pipeline Particle Counter will be rejected. The "Pipeline Particle Counter" is a "delayed" counter whose time delay is programmable from between 8 ms and 40 ms. Additionally, the "Post-Noise Time Indication Counter" will be reset with an incoming Coherence Indicator. 2) Without the presence of the Coherence Indicator, Pipeline all particle count events for the "Pre-Noise Indicator Time Window" of between 8 ms-40 ms. Mark Pipelined particle counts as valid after the "Pre-Noise Indicator Time Window" has expired. Reject all Pipelined particle counts if the Coherence Indicator becomes present before the "Pre-Noise Indicator time Window" has expired. 3) Every Coherence Indicator will reset the "Post-Noise Time Indicator Counter". This counter will stay in reset until the Coherence Indicator has expired. When the Coherence Indicator is removed, the "Post-Noise Time Indicator Counter" will count down through a programmed time of between10 ms and 50 ms. During this count down period all incoming particle events will be rejected.

EXAMPLE 2

Experimental Performance Evaluation

Laser light noise variation in available state-of-the-art diode-pumped solid-state (DPSS) lasers becomes a greater proportion of the SNR (Signal to Noise Ratio) in light scattering based Particle Counters as the push for detection of smaller and smaller particles in the fluid samples continue. As described above, changes in temperature of a laser cause a laser's cavity length to change, which in turn causes mode-hopping and unstable noise bursting in the laser's light intensity. In the following tests, laser noise was approximated by intentionally changing the temperature of the laser. To produce a changing temperature surrounding the instrument and its laser, a temperature controlled cabinet that uses a TEC (Thermal Electric Cooler) was used. The specific use of a cabinet that utilizes a TEC was important because unlike temperature controlled chambers that use refrigeration, the TEC does not generate Line Conducted electrical noise that might interfere with the interpretation of the effectiveness of the laser Noise Detection.

In an attempt to evaluate the effectiveness of the laser Noise Detection and Mitigation using optical ANDing, coupled with the subsequent data treatment when the ANDing hardware is or is not detecting laser optical noise, the following series of tests were performed. In the First Test, the Noise Detection and Mitigation circuitry was turned off while noise was approximated in the laser, resulting in temperature-induced noise in the data. In the Second Test, the Noise Detection and Mitigation circuitry was turned on while noise was approximated in the laser, resulting in elimination of count "flare-ups" at times of laser noise bursting. Further, in the Second Test, the effectiveness of the Noise Detection and Mitigation circuitry was demonstrated by turning it on, and then off, and then on again.

Figure 4:
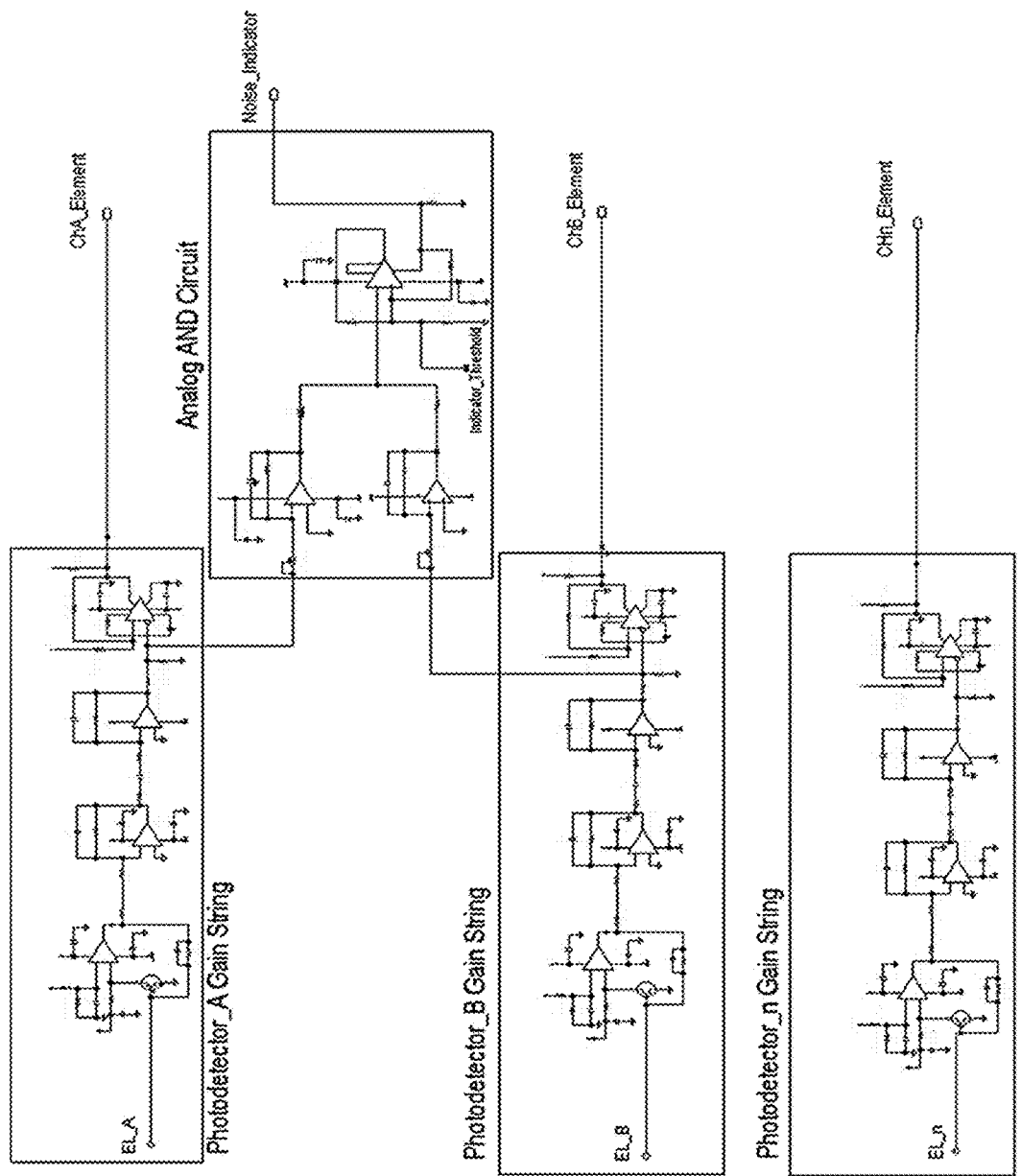
FIG. 4. Shows a very sensitive liquid particle counter circuit configured with the electrical realization of the Noise Detection and Mitigation circuitry.

First Test: Particle Counter without noise detection enabled and with changing temperature.
Test Preparation:

A very sensitive liquid particle counter was configured with the electrical realization of the Noise Detection and Mitigation circuitry shown in FIG. 4. The instrument's particle detection thresholds were purposely set to detect scattered light that was just over the molecular scatter from the volume of water viewed by the detectors. Allowances for enabling and disabling the circuitry were configured into the instrument.

The particle detection circuit shown in FIG. 4 was assembled into the instruments for this test and used for Laser Noise detection and Mitigation. In practice, the instrument uses a multi-element detector where the elements themselves only "view" their unique portion of the sample region and only detect real particles that move through these optically partitioned regions.

For simplicity, the circuit shown in FIG. 4 shows only three "gain" strings; A, B and n, but for practical, high performance particle counters; including the instruments used here, the number of individual elements in a detector typically exceed 10 and, for example, can be up to 24 (or more) separate elements. The gain strings amplify the photon-generated current from each element. Because of the required sensitivity, APD (Avalanche Photo diode) elements were used to take advantage of their internal photocurrent gain. The electrical output of each APD element is labeled as EL_A, EL_B and EL_n in the circuit in FIG. 4. The signal from each element picks-up gain as it moves through the gain string left-to-right. When a particle exists and is detected, each gain string indicates this existence through the output circuits labeled; ChA_Element, CHB_Element and CHn_Element. The outputs at this point have transitioned from analog current input signals to digital Voltage outputs.

For these instruments, an analog AND circuit was configured and attached to the A and B gain strings at a point just prior to point where the analog gain transforms into the digital signal of each. This AND circuit is outlined and labeled as "Analog AND Circuit" in the circuit in FIG. 4. There are two input amplifiers of the AND circuit that have their outputs tied together through separate isolation resistors. The two amplifiers monitor each gain string and will individually amplify their respective signals. Signals are generated in particle counters as a result of light being scattered by the particle as it passes through the focused laser light and the subsequent collection of this scattered light onto each photodetector element. The signals are "pulse" signals with FWHM (Full Width Half Maximum) value proportional to the size of the particle and its transit time through the laser beam.

When the particle counter is operating properly and without increased laser noise, particles will be detected individually by separate gain strings and will not be simultaneous with one another. These high performance particle counters are used to monitor very clean water systems which typically have very low particle concentrations. Because of this, the probability of simultaneous detections by multiple elements is extremely low.

In the circuit shown in FIG. 4, when the upper input amplifier of the AND circuit senses a pulse from gain string A, its output circuit tries to drive to a level that would exceed the "Indicator_Threshold" voltage and throw the Noise Indication. However, since there was no signal coming through gain string B, the lower input amplifier holds its output low. This high and low driving condition at the amplifier outputs hold the highest voltage level reached to below the Indicator_Threshold Voltage level and the Noise Indicator is held-off. Because there was not an indication, the real particle that triggers "ChA_Element" in the circuit above will be counted and reported. The same sequence of events happens if a real particle signal comes through B but not A. Here, the Noise Indication is again held-off and the particle trigger seen at "ChB_Element" is counted and reported.

When there is increased laser noise bursting, the beam intensity will increase momentarily as the noise "jumps" around. Since the individual elements are spaced side-by-side along the length of laser beam path a plurality, and optionally all. detector elements simultaneously sense the momentary increase in beam intensity. This momentary behavior produces pulses of light into all elements at once. During this laser noise event, both input amplifiers of the AND circuit drive their outputs high, and the previous high, low voltage contention; during the single real particle event, is removed and both the amplifier outputs push up above the Indicator_Threshold Voltage level and a Noise Indication is generated. This indication is a trigger that tells the CPLD (complex programmable logic device) to ignore all particle indications seen at any one of the A, B, or through n gain string outputs.

For the test instruments used in this study, the AND circuit was tied to only two element gain strings, but in other designs, there can be more than two inputs used. The user would need to scale the Indicator_Threshold Voltage level to account for any number of amplifier outputs driving this circuit node.

The circuit shown in FIG. 4 only covers the analog circuits involved in the detection and amplification of particle signals as well as the amplification and detection of the simultaneous events (noise events) coming through the element gain strings. All outputs shown to the right of the circuit couple into digital logic and particularly the CPLD mentioned before. The CPLD logs counts and passes the counts along to the reporting logic. As explained above in Example 1, the CPLD is also pipelining all data being received. This is in anticipation of a laser noise event. The particle is accepted if a "pre-noise indication time window" has expired. It is disregarded if signals are detected with coincidence from two or more detector elements as indicated by the Noise Indicator. This pipelining allows for detecting the build-up in laser activity just prior to the actual noise burst episode.

Additionally, the CPLD handles the timing involved in the disregarding of particle signals following a noise event. This is a programmable time window to allow the noise burst episode to settle back to normal noise levels before accepting particle events again.

In general, for the instruments used in the study, the noise detection sensitivity given the use of APD detectors and the element gain strings in the circuit shown in FIG. 4, allows for the detection of RMS noise levels of 0.15%.

The liquid Particle Counter was plumbed into a UPW (Ultra-Pure Water) source that was filtered to an average concentration contamination level of 2 particles/mL greater than 20 nm. The water source had a typical $D^{-3}$ water quality distribution, where a doubling in particle size is associated with a reduction in counts/mL by 8 times. For example, with 2 counts/mL at 20 nm, there are 2/8, or 0.25 counts/mL at 40 nm. This level of cleanliness of the water source is necessary so the expected small variation of particle counts from sample to sample registered by the instrument during quiet laser periods can be compared to the registered counts when there is laser noise which adds false counts to the real particle count level.

Figure 5:
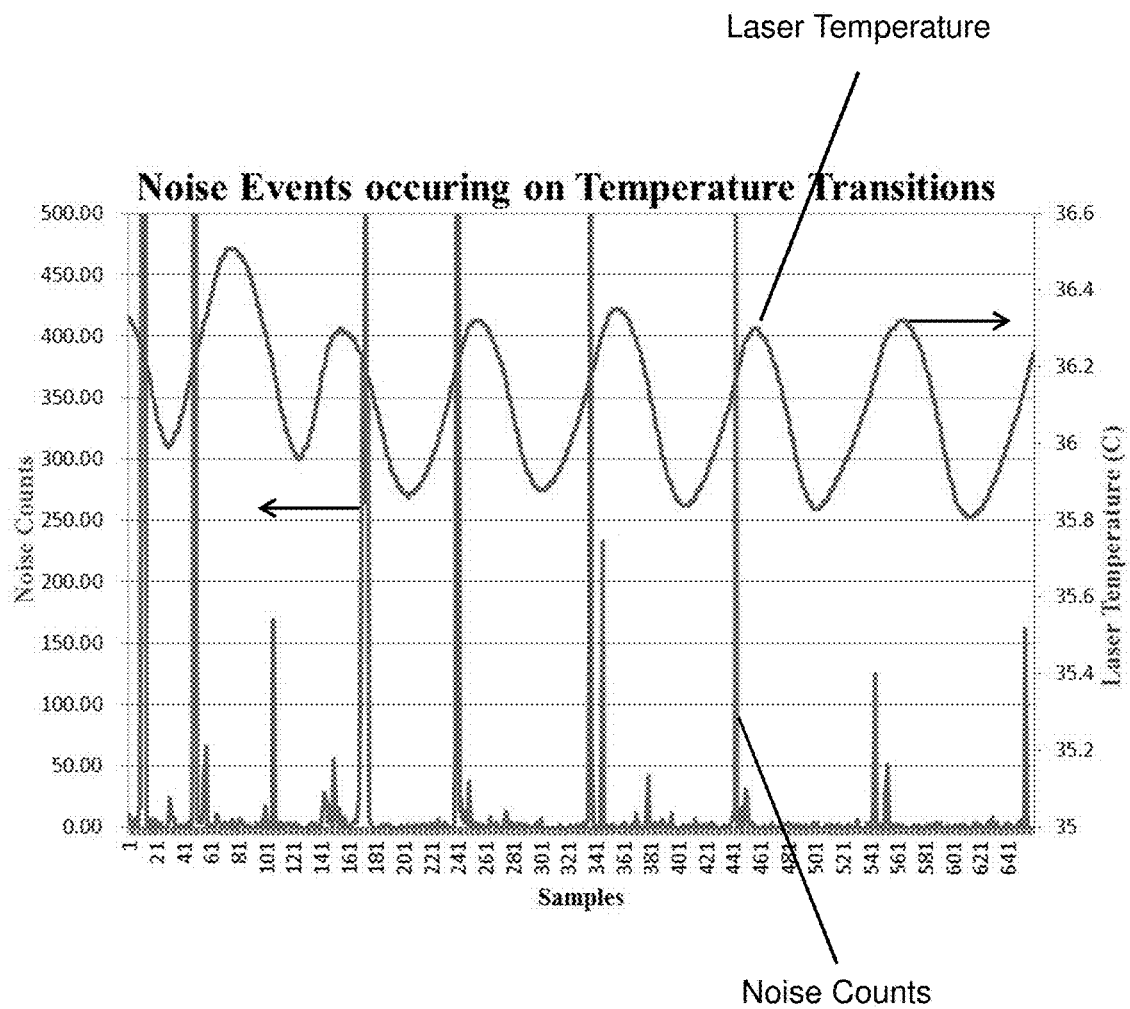
FIG. 5. Shows the counting of events (light scatter, or otherwise increased light intensity) by the instrument through approximately 657 samples, and a continual trace of the cabinet temperature.

FIG. 5 shows the counting of events (light scatter, or otherwise increased light intensity) by the instrument thru approximately 657 samples, and a continual trace of the cabinet temperature. Apparent in the plot is the association of the increase in the number of occurrences at the time the laser is experiencing changing temperature. Close examination of the magnitude of the changing laser temperature, shows that a change of only 0.5° C. is enough to cause the laser's light intensity to burst. Because the detectors are very high speed with high Responsivity, these positive intensity impulses are enough to create false counts in the instrument's detection circuitry and reported data. It is this sensitivity to temperature change that makes detection of very small particles, without false counting, difficult in light scattering based particle counters.

With the Particle Counter being a laser light scattering based design, means the noise occurrences, shown as the lower trace in FIG. 5 will be reported as particle counts. These transition counts are false counts and the real particle level of the water being sampled is the low level activity in between the vertical reported (noise) traces. In the figure, the vertical false counts can exceed 500 counts per sample as the laser's light continues to burst from several milliseconds to a couple hundred milliseconds. The real or actual particle count level is below 50 counts per sample and averages approximately 2 counts per sample.

Second Test: Particle Counter with noise detection enabled and with changing temperature.

The same Particle Counter used in the First test was used here. The difference in the instrument was that the noise detection circuitry was enabled for this test.

It was shown in the first test that if the Particle Counter's detection threshold is tuned sensitive enough, the changes in the laser's positive going light impulses, or noise bursts, even with small temperature changes can be viewed and detected.

Here in test two, the temperature was varied over a much larger range, when compared to test one, for evaluation of the effectiveness of the Noise Detection and Mitigation circuitry. In addition to the count data and temperature data in the plot, the noise indicator; indication that two ANDed detectors have simultaneously witnessed a positive laser intensity impulse has been added and traced through the samples.

As described, each one of the multiple detector elements views "their" portion of the total viewing volume separately from any of the other elements. Real particles are witnessed by any single element only when the particle passes through that element's viewing portion. By ANDing two or more elements, the laser noise, which is seen by all elements simultaneously can be distinguished from real particles. To be interrupted as noise, one element AND another or another several, need to detect a positive light scatter impulse, which sets the indicator. If only one element detects a light scatter impulse, the AND function fails and the impulse is recorded as a real particle. In very clean water systems where high sensitivity Particle Counters are used, the probability of two real particles passing through the viewing area of two separate elements is vanishingly small.

Figure 6:
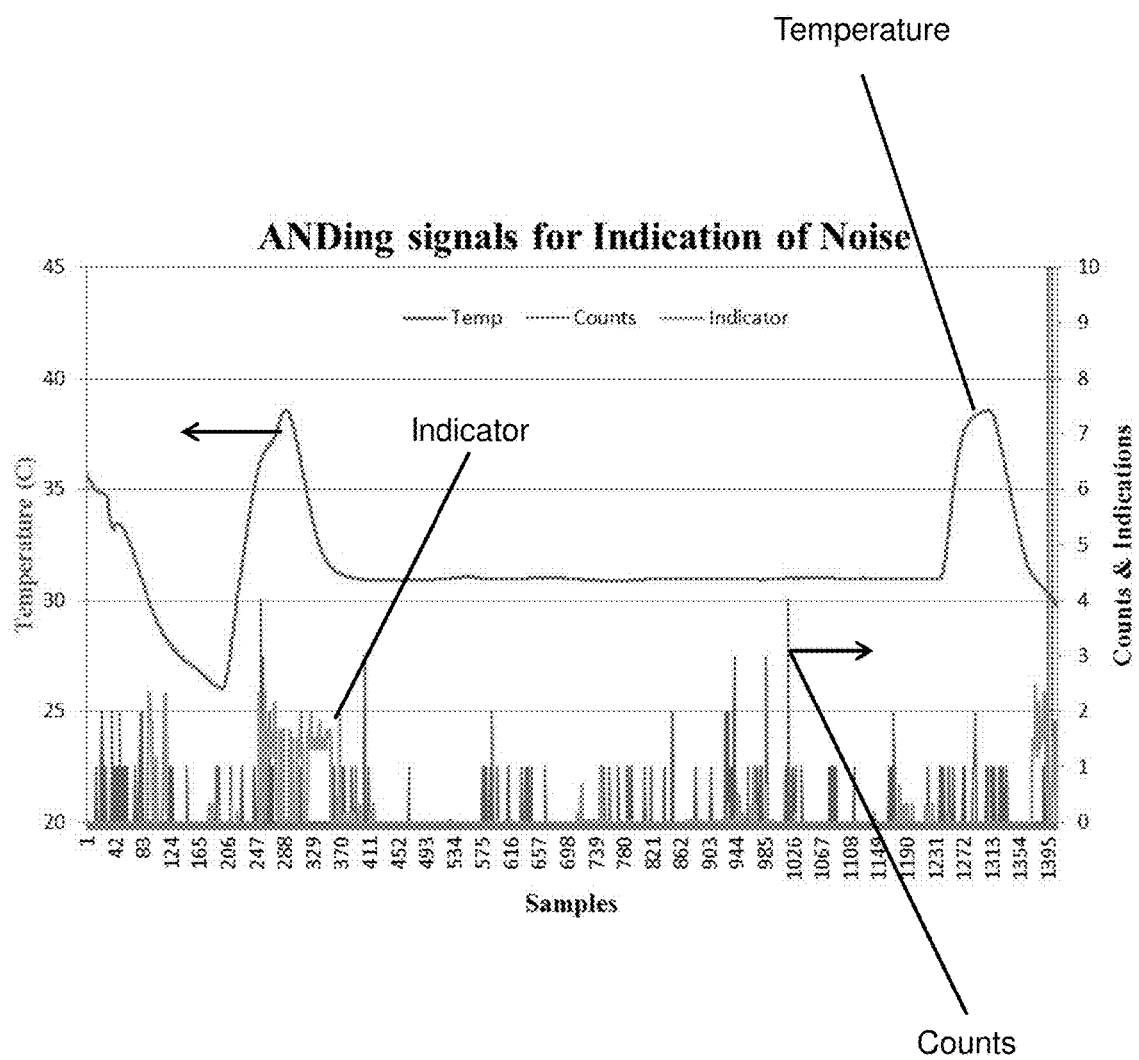
FIG. 6. Shows the counting of events (light scatter, or otherwise increased light intensity) by the instrument, and a continual trace of the cabinet temperature.

FIG. 6 shows the counting of events (light scatter, or otherwise increased light intensity) by the instrument, and a continual trace of the cabinet temperature. The overall temperature ranges between approximately 25.2 C and 38 C or 7.8 C at each end of the plot with an almost steady state temperature section throughout the center of the plot. The "Counts" trace is count data coming in with each sample update. The AND circuitry has been enabled in the test instrument and the indicator activity has been added to the plot and is shown as the "indicator" trace. At the left and right ends of the plot, the indicator activity is occurring more frequently with changing temperature as compared to the center section of the plot where the temperature is steady to within ±0.25 C. This increased indicator activity is witness to the laser's internal cavity experiencing thermal changes and creating burst noise in its output beam. The burst noise is seen by one or more elements simultaneously and so the AND function passes and an indication is flagged. In the instrument's firmware, when there is an indication, there is no recording of particle data and so false counts are eliminated. Even in the center section of the plot there are discrete samples where the indicator becomes active. If not for the ANDing circuitry and indicator, these laser noise periods would have been recorded as spiking particle data as was seen in FIG. 5.

An inspection of the reported particle count data can be used as a way of interpreting the accuracy and benefits of the optical ANDing circuitry. What would normally be expected for reported data from a system that has reached a steady state (cleaned-up to the systems baseline contamination level), with constant concentration, is that the Standard Deviation of the data set should be very close to the Square Root of the mean of the data. Looking at the plot in FIG. 6 as three separate segments; left, center and right, the calculated mean of the particle counts together with the calculated Std. Dev. for each segment is shown below.

| Left Segment | 0.164286 |
| --- | --- |
|  | 0.474298 |
| Center Segment | 0.100906 |
|  | 0.374251 |
| Right Segment | 0.115942 |
|  | 0.335717 |

From above, with the data average for the left segment being 0.164286, then $\sqrt{0.164286}=0.4053$. The calculated standard deviation from above was 0.474298; very close to theoretical.

Again from above, with the data average for the center segment being 0.100906, then $\sqrt{0.100906}=0.3177$ The calculated standard deviation from above was 0.374251; again, very close to theoretical.

For the right segment above, with the data average for the left segment being 0.115942, then $\sqrt{0.115942}=0.3405$. The calculated standard deviation from above was 0.335717; here again, very close to theoretical.

With the data set variance being very close to theoretical for times when the AND circuitry is indicating laser noise; left and right segments of the plot in FIG. 6, and very nearly the same as when there is low activity; center segment, is witness that the Noise Detection and Mitigation circuitry is functioning as intended and reporting real particles when there is no laser noise periods and only eliminating those laser noise intensity bursts that would otherwise be reported as particle counts. If fact there is no increase in the variance in the data set when the ANDing circuitry is eliminating false count as compared to when the laser is quiet and the instrument is reporting only real particles.

Figure 7:
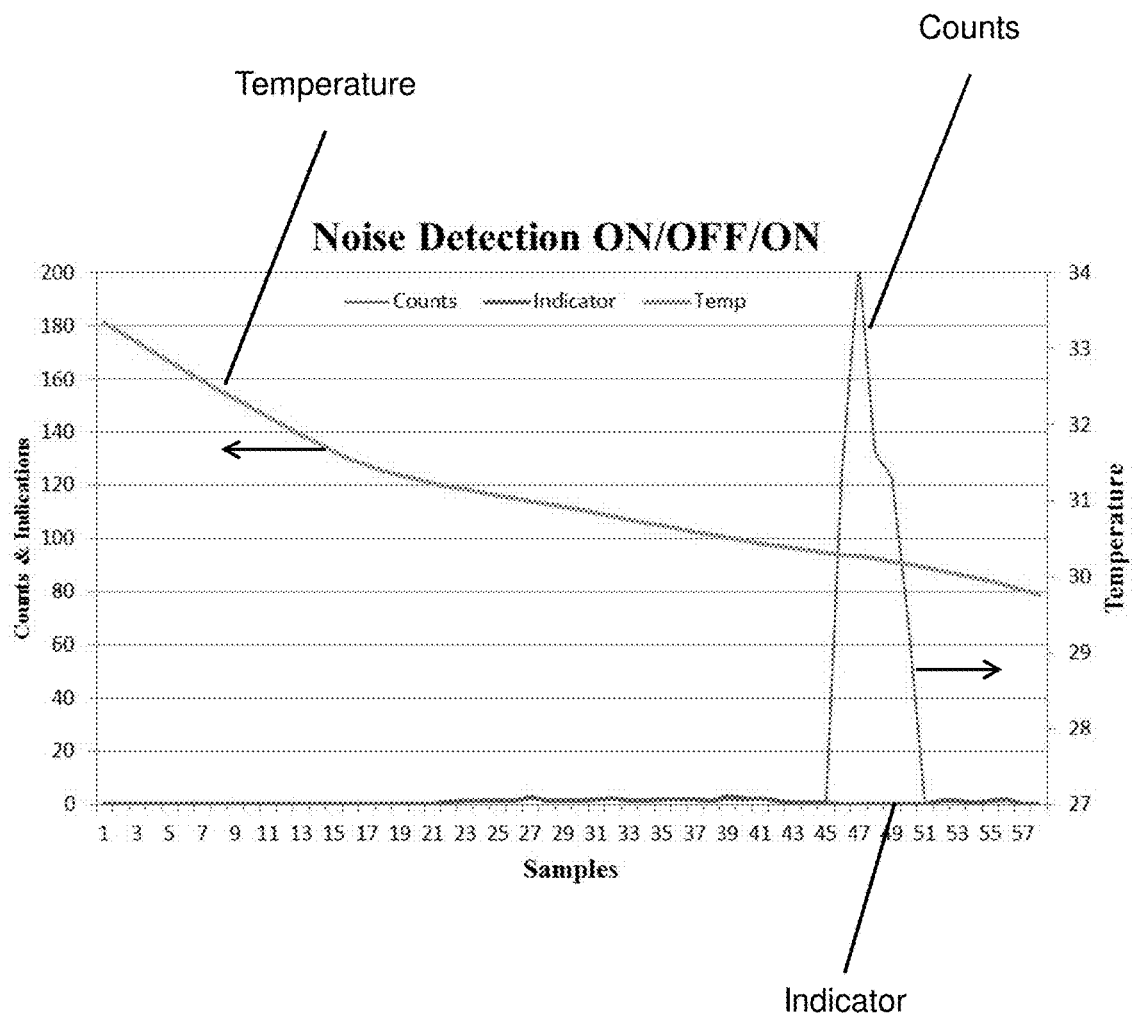
FIG. 7. Shows an expanded view of the right side of FIG. 6, showing the counting of events (light scatter, or otherwise increased light intensity) by the instrument, and a continual trace of the cabinet temperature.

The very right side of the plot from FIG. 6 is expanded and shown in FIG. 7. In the figure, the temperature is on a downward swing and the indicator is firing (low level "Indicator" traces) from about data point 21 to where the noise mitigation is turned off at data point 45. With noise mitigation off, the indicator is ignored and all particle counting is accepted and reported even when seen simultaneously over multiple detector elements. As can be seen there were approximately 200 false counts as a result of the laser noise bursting due to the changing temperature. At data point 51 the noise mitigation was turned on again where the indicator firings were recoded and the false counts removed. This last ON and OFF test was a simple way of verifying the system was still functioning and trapping false counts.

The noise mitigation scheme deliberately indicates when the laser noise is bursting and counts need to be ignored and as a consequence provides an indication when not present, that the laser is quiet and all counts should be accepted.

The data results show the noise detection and mitigation scheme is providing the necessary elimination of count "flare-ups" at times of laser noise bursting.

EXAMPLE 3

Array Detector Embodiments for Laser Noise Detection and Mitigation

A range of array detector geometries and related signal processing methods are useful in the present methods and systems.

Detector Spacing

In methods and systems of embodiments of the present design, multiple detector elements are used to detect individual real particles as these particles pass through spatially separated viewing regions being witnessed by each of the separate elements.

For very small of particle sizes; e.g., having cross sectional dimensions of approximately 20 nm, the collected partial scattering of light from these particles and the amount of photon energy in each of these scattering events is enough to generate sufficient photon-generated current above the molecular background scattering and be recorded as a particle event when a high percentage of the imaged spot falls inside a single element without some of the photon energy falling into a separating region between elements, or when the image partially overlaps the edges of two adjacent elements. On the other hand, for particles larger than approximately 70 nm, the amount of energy in a scattering event is enough to be recorded as a particle event even though the imaged spots cross adjacent element boundaries. Typical post element signal processing may provide for elimination of redundant particle counting for these larger but real particle sizes. In embodiments, however, because of this cross-coupling of scattered spot images by larger particles, there may become a limit in the minimum element separation when these elements are used in laser noise detection and mitigation.

In some 20 nm particle counters employing noise detection and mitigation, for example, a counting channel sizes covers sizes 20 nm through 100 nm. With an example instrument designed to size and count 100 nm particles, the selected elements from the array detector to be used for laser noise detection may have enough spatial separation between them to eliminate the potential of cross-coupling the scattered particle spot images from real 100 nm particles into both selected elements. A practical concern, for example, is that without proper or sufficient separation, the selected elements can see the 100 nm image simultaneously and, thereby, provide a false indication of laser noise to the operating firmware. As the noise detection and mitigation functions, each of these false indications may result in the elimination of larger particle size counts in the reported data.

In embodiments, choice of the separation distance of the noise detecting elements has no significant adverse effect on the laser noise detection and mitigation as long as all elements of the array detector are viewing the light source simultaneously.

In certain embodiments, however, there may exist physical limits on element separation due in part to the geometry of the Sample Viewing cell and the available commercial array detectors. In the very rare occurrence where there are a very large numbers of larger particles flowing through the sampling region, the scattering can turn from a typical single scattering event above the background molecular scatter and become Bulk Scattering in nature. During these rare events, all elements, including the ones used in the noise detection and mitigation can receive sufficient scattering to register a laser noise event. In such a case, the noise detection and mitigation may inherently sets a somewhat maximum particle concentration for the instrument, which would typically be well above what is normal for many applications of interest including clean room and/or aseptic processing applications.

Detector Element Thresholds

In the description of this Example, the mention of threshold or detection level and signal are represented as voltage levels in an example Particle Counter and laser noise detection circuity.

In an embodiment, the detection of particle events is determined by a threshold that is set to 1.5:1 to 2.0:1 over the Particle Counter System noise which includes and is dominated by the sample's molecular scatter. The laser noise detection is set in some embodiments through the use of a threshold. When noise detection is used in very small size sensitive Particle Counters where the Particle Counter's SNR (signal to noise ratio) is on the order of 1.5:1 to 2.0:1, this noise threshold level may be very close to the particle size threshold level to provide enough laser noise sensitivity. In some embodiments, the electrical points of detection of the laser noise threshold and particle threshold are different though the signal paths and have different signal and group delays as well as phase shift. Original settings of the laser noise detection threshold may be set to levels where the delay in noise detection to particle detection is inside the signal data 8 ms to 40 ms pipelining. The pipelining allows noise trapping even as the noise starts to build by holding accumulated counts ahead of the buildup in noise and actually overtakes the noise detection threshold. In some embodiments, if there are counts inside the 8 ms to 40 ms pipeline when laser noise detection occurs, those counts may be disregarded.

In some embodiments, to improve the detection of noise and ensure the detection is within the 8 ms to 40 ms pipeline window, the bandwidths of the noise detector amplifiers of the Analog AND circuit in FIG. 4 may be increased. The nature of the laser noise is chaotic and the frequency spectrum in itself chaotic. In some embodiments, for example, the bandwidth of the Analog AND amplifiers are increased to provide useful performance for a given application. Since delay is approximated by 1/BWR where BWR is the bandwidth in radians/second, it may be that the delay introduced by the Analog AND amplifiers is the same, if not shorter, than the delay introduced in the downstream particle signal path. In some embodiments, the Analog AND amplifiers have higher bandwidth limiting then the remaining signal path elements leading up to the particle signal detection node. Selection of the bandwidth may be determined by comparing the amplifier's slew rate to detection threshold, with the 8 ms to 40 ms window. To ensure detection inside the 8 ms to 40 ms window, the Analog AND amplifier limiting bandwidth is increased relative to the particle signal path bandwidths. This increased bandwidth is useful, for example, in systems and methods for a 20 nm Particle Counter.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method for detecting particles in a fluid flow, said method comprising the steps of:
   providing said fluid flow having said particles;
   exposing said fluid flow to a beam of electromagnetic radiation from a laser, thereby generating scattered or emitted electromagnetic radiation;
   collecting and directing said scattered or emitted electromagnetic radiation from a viewing region onto a plurality of detector elements; wherein each detector element is positioned to receive said scattered or emitted electromagnetic radiation from a different portion of said viewing region;
   detecting said electromagnetic radiation directed onto said plurality of detector elements, wherein each of said detector elements generates independent output signals;
   comparing output signals from at least two different detector elements to discriminate output signals corresponding to a particle detection event from output signals corresponding to a laser noise event;
   analyzing output signals corresponding to said detection event; and
   identifying said laser noise event, wherein said laser noise event is identified when the output signals of each of at least two non-adjacent detector elements is independently equal to or greater than a threshold value; thereby detecting said particles in said fluid flow.

2. The method of claim 1, wherein an increase in the magnitude of said output signals of only a single detector element or a subset of adjacent detector elements is indicative of said particle detection event.

3. The method of claim 1, wherein said step of collecting and directing said scattered or emitted electromagnetic radiation from said viewing region is provided using a system of optics for focusing said scattered or emitted electromagnetic radiation from said viewing region on to said plurality of detector elements.

4. The method of claim 3, wherein the system of optics and/or the physical dimensions, positions or both of detector elements are such that only a subset of detector elements of the plurality receives said scattered or emitted electromagnetic radiation corresponding to said particle detection event.

5. The method of claim 3, wherein the system of optics and/or the physical dimensions, positions or both of detector elements are such that all the detector elements of the plurality receive said scattered or emitted electromagnetic radiation corresponding to said laser noise event.

6. The method of claim 3, wherein said plurality of detectors comprise a detector array positioned in optical communication with said system of optics such that each element of the array receives scattered or emitted electromagnetic radiation from a different portion of said viewing region.

7. The method of claim 6, wherein said detector array is a one dimensional array comprising 2 to 20 detector elements.

8. The method of claim 7, wherein each of said detector elements of said one dimensional array independently has an active area characterized by lateral dimensions selected from the range of 410 µm to 440 µm.

9. The method of claim 7, wherein adjacent detector elements of said one dimensional array are separated from each other by a distance selected from the range of 60 µm to 90 µm.

10. The method of claim 1, wherein said laser is a solid state laser or diode laser.

11. The method of claim 1, wherein said laser noise event corresponds to a change in the radiative output of said laser, thereby generating said scattered or emitted electromagnetic radiation from said viewing region having a substantially uniform spatial distribution of intensities.

12. The method of claim 1, wherein said particle detection event corresponds to a particle passing through a beam of electromagnetic radiation, thereby generating said scattered or emitted electromagnetic radiation from said viewing region having a nonuniform spatial distribution of intensities.

13. The method of claim 12, wherein said step of comparing output signals from at least two different detector elements comprises characterizing the spatial distribution of intensities of said scattered or emitted electromagnetic radiation to discriminate output signals corresponding to a particle detection event from output signals corresponding to a laser noise event.

14. The method of claim 1, further comprising identifying said particle detection event, wherein said particle detection event is identified when the output signals of only a single detector element or subset of adjacent detector elements is independently equal to or greater than a threshold value.

15. The method of claim 14, wherein said threshold value for a given detector element is equal to 1.5:1 to 2.0:1 times the standard deviation of the noise of the given detector element of said array.

16. The method of claim 1, wherein said laser noise event is identified when the output values of each of all detector elements is independently equal to or greater than a threshold value.

17. The method of claim 1, wherein said threshold value is independently set for each detector element.

18. The method of claim 17, wherein said threshold value for a given detector element is equal to 1.5:1 to 2.0:1 times the standard deviation of the noise of the given detector element of said array.

19. The method of claim 1, further comprising, upon identification of a laser noise event, monitoring the output signals for all detector elements to identify a change in output values for at least two detector elements independently greater than or equal to a factor of 1.5:1 to 2.0:1 times the standard deviation of the noise of the given detector element of said array.

20. The method of claim 1, further comprising the steps of:
storing said output signals for all detector elements for a preselected time period; and
analyzing said stored output signals in the event that no laser noise event is identified or discarding said stored output signals in the event that said laser noise event is identified.

21. The method of claim 1, further comprising, upon identification of a laser noise event, waiting for a preselected time period prior to identifying a particle detection event.

22. The method of claim 1, wherein said fluid is ultrapure water, Sulfuric Acid ($H_2SO_4$), Hydrofluoric Acid (HF), Hydrochloric Acid (HCl), Ammonium Hydroxide ($NH_4OH$), Hydrogen Peroxide ($H_2O_2$) or Isopropyl Alcohol ($C_3H_7OH$).

23. The method of claim 1, further comprising a step of counting said particles, wherein said step of comparing output signals from at least two different detector elements to discriminate output signals corresponding to said particle detection event from output values corresponding to said laser noise event enables a decrease in the occurrence of false counts.

24. The method of claim 1, further comprising controlling a temperature of said laser to reduce laser noise, wherein said controlling is performed with a thermoelectric cooler (TEC).

25. An optical particle analyzer comprising:
a laser for generating a beam of electromagnetic radiation;
a flow chamber for flowing a fluid containing particles along a flow direction and through the beam of electromagnetic radiation, thereby generating scattered or emitted electromagnetic radiation;
an optical collection system for collecting and directing said scattered or emitted electromagnetic radiation from a viewing region onto a plurality of detector elements;
said detector elements for detecting said electromagnetic radiation and generating independent output signals; and wherein each detector element is positioned to receive scattered or emitted electromagnetic radiation from a different portion of said viewing region; and
a signal processing system operationally connected to said detector elements for:
comparing output signals from at least two different detector elements to discriminate output signals corresponding to a particle detection event from output signals corresponding to a laser noise event;
analyzing said output signals corresponding to said detection event; and
identifying said laser noise event; wherein said laser noise event is identified when the output signals of each of at least two non-adjacent detector elements is independently equal to or greater than a threshold value.

26. A method of distinguishing particle scattering from laser noise in an optical particle analyzer, said method comprising the steps of:
providing a fluid flow having particles to said optical particle analyzer;
exposing said fluid flow to a beam of electromagnetic radiation from a laser,
wherein interaction between said fluid flow and said beam generates scattered or emitted electromagnetic radiation;
collecting and directing said scattered or emitted electromagnetic radiation from a viewing region onto a plurality of detector elements; wherein each detector element is positioned to receive said scattered or emitted electromagnetic radiation of from a different portion of said viewing region;
detecting said electromagnetic radiation directed onto said plurality of detector elements, wherein each of said detector elements generates independent output signals;
comparing output signals from at least two nonadjacent different detector elements to discriminate output signals corresponding to a particle detection event from output signals corresponding to a laser noise event; and
identifying said laser noise event; wherein said laser noise event is identified when the output signals of each of at least two non-adjacent detector elements is independently equal to or greater than a threshold value.

27. A method for detecting particles in a fluid flow, said method comprising the steps of:
providing said fluid flow having said particles;
exposing said fluid flow to a beam of electromagnetic radiation from a laser, thereby generating scattered or emitted electromagnetic radiation;
collecting and directing said scattered or emitted electromagnetic radiation from a viewing region onto a plurality of detector elements; wherein each detector element is positioned to receive said scattered or emitted electromagnetic radiation from a different portion of said viewing region;
detecting said electromagnetic radiation directed onto said plurality of detector elements, wherein each of said detector elements generates independent output signals;
comparing output signals from at least two different detector elements to discriminate output signals corresponding to a particle detection event from output signals corresponding to a laser noise event;
analyzing output signals corresponding to said detection event, thereby detecting said particles in said fluid flow;
identifying said laser noise event;
storing said output signals for all detector elements for a preselected time period; and
analyzing said stored output signals in the event that no laser noise event is identified or discarding said stored output signals in the event that said laser noise event is identified.

28. A method for detecting particles in a fluid flow, said method comprising the steps of:

providing said fluid flow having said particles;

exposing said fluid flow to a beam of electromagnetic radiation from a laser, thereby generating scattered or emitted electromagnetic radiation;

collecting and directing said scattered or emitted electromagnetic radiation from a viewing region onto a plurality of detector elements; wherein each detector element is positioned to receive said scattered or emitted electromagnetic radiation from a different portion of said viewing region;

detecting said electromagnetic radiation directed onto said plurality of detector elements, wherein each of said detector elements generates independent output signals;

comparing output signals from at least two different detector elements to discriminate output signals corresponding to a particle detection event from output signals corresponding to a laser noise event;

analyzing output signals corresponding to said detection event, thereby detecting said particles in said fluid flow;

identifying said laser noise event; and upon identification of a laser noise event, waiting for a preselected time period prior to identifying a particle detection event.

29. The method of claim 28 wherein said preselected time period is selected from the range 10 ms to 50 ms.

* * * * *